(12) United States Patent
Sin et al.

(10) Patent No.: US 11,259,796 B2
(45) Date of Patent: Mar. 1, 2022

(54) BIO PARACENTESIS NEEDLE AND METHOD FOR MANUFACTURING THE SAME

(71) Applicant: 21 Century Medical Co. Ltd., Gwangju (KR)

(72) Inventors: Mi Hyang Sin, Gwangju (KR); Jae Won Yoo, Gwangju (KR)

(73) Assignee: 21 Century Medical Co. Ltd., GwangJu (KR)

( * ) Notice: Subject to any disclaimer, the term of this patent is extended or adjusted under 35 U.S.C. 154(b) by 755 days.

(21) Appl. No.: 15/046,702

(22) Filed: Feb. 18, 2016

(65) Prior Publication Data
US 2016/0296228 A1    Oct. 13, 2016

(30) Foreign Application Priority Data

Apr. 9, 2015    (KR) .......................... 10-2015-0050468

(51) Int. Cl.
*A61B 17/06*    (2006.01)
*A61B 10/00*    (2006.01)
(Continued)

(52) U.S. Cl.
CPC .... *A61B 17/06066* (2013.01); *A61B 10/0045* (2013.01); *B21G 1/08* (2013.01);
(Continued)

(58) Field of Classification Search
CPC ........ A61B 2017/047; A61B 2017/048; A61B 2017/06019; A61B 2017/06023;
(Continued)

(56) References Cited

U.S. PATENT DOCUMENTS 3,007,471 A * 11/1961 McClure, Jr. ...... A61B 10/0266
                                                        600/567
5,312,422 A *  5/1994 Trott .................. A61B 17/0469
                                                        604/272
(Continued)

FOREIGN PATENT DOCUMENTS

JP    S55-171047 U    5/1979
JP    2002-291883 A   10/2002
(Continued)

*Primary Examiner* — Sarah W Aleman
(74) *Attorney, Agent, or Firm* — Novick, Kim & Lee, PLLC; Sang Ho Lee

(57) ABSTRACT

A bio paracentesis needle includes a tube-shaped body having a hollow portion through which a suture is inserted, an insertion portion formed at an end of the body to cut skin and insert the body, and at least one removal cut to an inside of the body to remove waste under the skin when the body is inserted. The insertion portion includes a first inclined edge having a diagonal surface inclined downward in a direction from a first end of the both to the hollow portion, a second inclined edge having a diagonal surface inclined upward from a second end of the body to the first inclined edge, the second end being positioned opposite the first end, and a third inclined edge has a diagonal surface inclined downward in a direction from an end of the first inclined edge to the second inclined edge.

8 Claims, 5 Drawing Sheets

(51) Int. Cl.
*B21G 1/08* (2006.01)
*A61B 17/00* (2006.01)

(52) U.S. Cl.
CPC .............. *A61B 2010/0077* (2013.01); *A61B 2017/00526* (2013.01); *A61B 2017/00792* (2013.01); *A61B 2017/06052* (2013.01)

(58) Field of Classification Search
CPC ........... A61B 2017/06028; A61B 2017/06042; A61B 2017/06047; A61B 2017/06071; A61B 2017/06085; A61B 2017/00349; A61B 2017/061; A61B 2017/06052; A61B 17/06; A61B 17/06004; A61B 17/0469; A61B 17/06066; A61B 17/3401; A61B 10/0045; A61B 2010/0077; A61B 2017/00792; A61B 10/0275; A61B 17/32053; A61B 17/320708; A61B 2017/3454; A61B 2017/320064; A61B 2017/320741; A61M 5/3286; A61M 5/3291; B21G 1/08
See application file for complete search history.

(56) References Cited

U.S. PATENT DOCUMENTS

| | | | | |
|---|---|---|---|---|
| 5,342,397 A | * | 8/1994 | Guido | A61B 17/06066 606/222 |
| 5,405,354 A | * | 4/1995 | Sarrett | A61B 17/0469 112/169 |
| 5,499,991 A | * | 3/1996 | Garman | A61B 17/0483 606/148 |
| 9,955,956 B2 | * | 5/2018 | Asaoka | A61B 1/05 |
| 2004/0030303 A1 | * | 2/2004 | Prais | A61M 5/3202 604/272 |
| 2004/0249393 A1 | * | 12/2004 | Weisel | A61B 17/06109 606/144 |
| 2004/0249394 A1 | * | 12/2004 | Morris | A61B 17/0469 606/144 |
| 2005/0021055 A1 | * | 1/2005 | Toubia | A61B 17/0057 606/144 |
| 2012/0123448 A1 | * | 5/2012 | Flom | A61B 17/0483 606/144 |
| 2013/0218173 A1 | * | 8/2013 | Weisel | A61B 17/0469 606/144 |
| 2013/0237879 A1 | * | 9/2013 | Takeuchi | A61B 10/0275 600/567 |

FOREIGN PATENT DOCUMENTS

| | | |
|---|---|---|
| JP | 2007-501676 A | 2/2007 |
| JP | 2008-526335 A | 7/2008 |
| JP | 2009-233028 A | 10/2009 |
| JP | 2013-141488 A | 7/2013 |
| JP | 2014-039720 A | 3/2014 |
| KR | 2000-0068025 A | 11/2000 |
| KR | 10-2005-0074870 A | 7/2005 |
| KR | 10-1405071 A | 6/2014 |
| KR | 10-1571291 B1 | 11/2015 |
| WO | 2004/045686 A1 | 6/2004 |
| WO | 2014/145724 A2 | 9/2014 |

* cited by examiner

BIO PARACENTESIS NEEDLE AND METHOD FOR MANUFACTURING THE SAME

CROSS-REFERENCE TO RELATED APPLICATIONS

This patent application claims priority under 35 U.S.C. § 119 to Korean Patent Application No. 10-2015-0050468, filed on Apr. 9, 2015, in the Korean Intellectual Property Office, the disclosure of which is incorporated by reference herein in its entirety.

TECHNICAL FIELD

Embodiments of the present disclosure concern needles and methods for manufacturing the same, and more specifically, to bin paracentesis needles with a sharp blade-shaped edge or tip and methods for manufacturing the same.

DISCUSSION OF RELATED ART

Paracentesis needles have various applications, such as infection of medicine or obtaining cerebrospinal fluid. Paracentesis needles for plastic surgery ma inject sutures into the skin to spread skin wrinkles.

Conventional paracentesis needles for plastic surgery can be inserted at a predetermined angle into a deep target but not inserted shallow along the skin wrinkles.

SUMMARY

According to an embodiment of the present disclosure, a bio paracentesis needle comprises a tube-shaped body having a hollow portion through which a suture is inserted, an insertion portion formed at an end of the body to cut skin and insert the body, and at least one removal cut to an inside of the body to remove waste wider the skin when the body is inserted. The insertion portion may include a first inclined edge having a diagonal surface inclined downward in a direction from a first end of the body to the hollow portion, a second inclined edge having a diagonal surface inclined upward from a second end of the body to the first inclined edge, the second end being positioned opposite the first end, and a third inclined edge baying a diagonal surface inclined downward in a direction from an end of the first inclined edge to the second inclined edge. A first surface of the removal cut is formed perpendicular to a longitudinal direction of the body, and a second surface of the removal cut may be formed to be inclined in an opposite direction of the insertion portion. Alternatively, the second surface of the removal cut may be formed to be inclined in a direction of the insertion portion.

The removal cut may be shaped as a "V."

An end where the second inclined edge and the third inclined edge meet may he shaped as a straight line.

Two opposite sides of the second inclined edge and the third inclined edge may be rounded towards the hollow portion.

The body may be curved or bent.

According to an embodiment of the present disclosure, a method for manufacturing a bio paracentesis needle having a body shaped as a tube and a hollow portion through which a suture is inserted comprises a first cutting step of forming a first inclined edge by cutting the body in a direction inclined downward from a first end of the body to the hollow portion, a second cutting step of cutting the first inclined edge perpendicular to an outer circumferential surface of the body, a third cutting step of forming a second inclined edge by cutting the body in a direction inclined upward from a second end of the body to the first inclined edge, the second end positioned opposite the first end, a fourth cutting step of forming a third inclined edge by cutting the body in a direction inclined downward from the hollow portion to the second inclined edge, and a fifth cutting step of forming a removal cut in a direction from the outer circumferential surface to the hollow portion before or after any one of the first cutting step, the second cutting step, the third cutting step, and the fourth cutting step. A first surface of the removal cut is formed perpendicular to a longitudinal direction of the body, and a second surface of the removal cut may be formed to be inclined in an opposite direction of the first inclined edge.

The method may further comprise a rounding step of rounding two opposite sides of the second inclined edge and the third inclined edge towards the hollow portion.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF EMBODIMENTS

Hereinafter, exemplary embodiments of the inventive concept will be described in detail with reference to the accompanying drawings, The inventive concept, however, may be modified in various different ways, and should not be construed as limited to the embodiments set forth herein. As used herein, the singular forms "a," "an," and "the" are intended to include the plural forms as well, unless the context clearly indicates otherwise. It will be understood that when an dement or layer is referred to as being on "connected to," "coupled to," or "adjacent to" another element or layer, it can be directly on, connected, coupled, or adjacent to the other element or layer, or intervening elements or layers May be present. The terms "first" and "second" are used to distinguish an element from another and embodiments of the present disclosure are not limited thereby or thereto.

Figure 1:
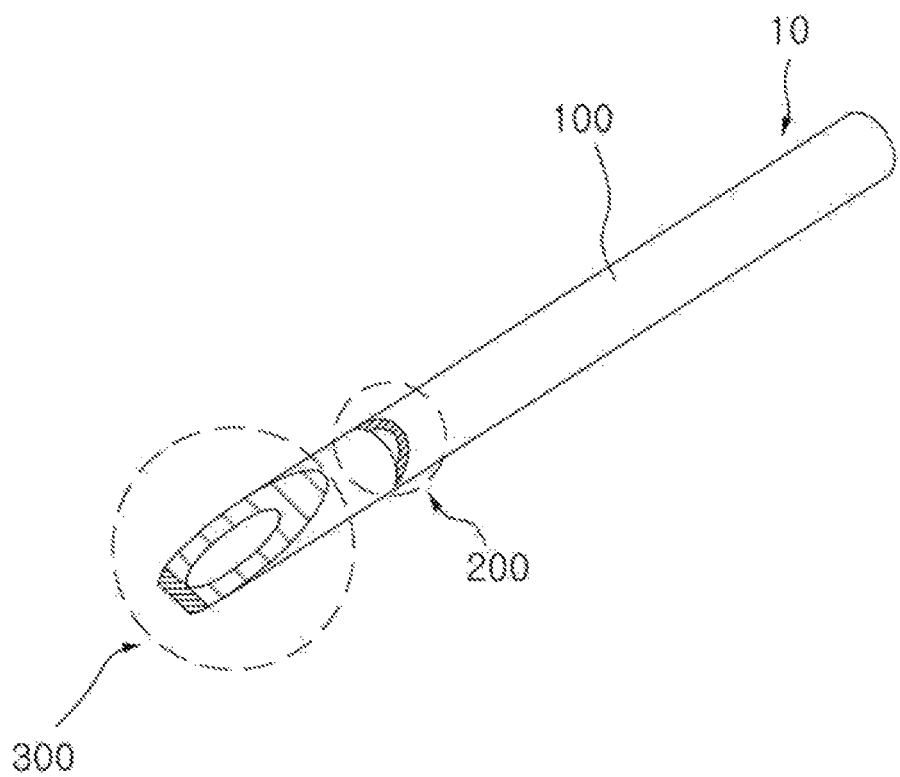
FIG. 1 is a perspective view illustrating a bin paracentesis needle according to an embodiment of the present disclosure.
Figure 2:
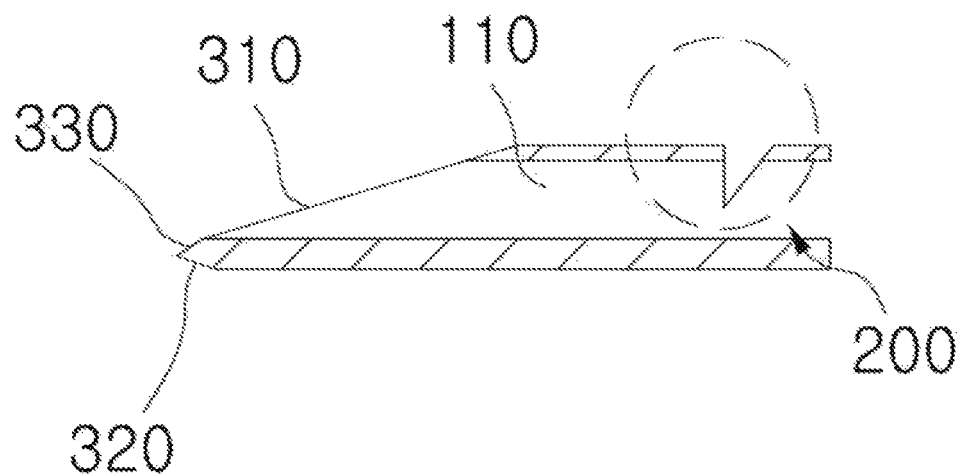
FIG. 2 is a cross-sectional view illustrating a bio paracentesis needle as illustrated in FIG. 1.

FIG. 1 is a perspective view illustrating a bio paracentesis needle according to an embodiment of the present disclosure. FIG. 2 is a cross-sectional view illustrating a bio paracentesis needle as illustrated in FIG. 1.

Referring to FIGS. 1 and 2, the bio paracentesis needle 10 may include a body 100. The body 100 may be shaped as a thin, long tube or pipe. The body 100 may have various lengths and diameters depending on where the procedure is performed. The body 100 may have a shaped curved or bent at a predetermined angle. The body 100 may be formed of a metal or elastic material. The body 100 may include a hollow portion 110, a removal cut 200, and an insertion portion 300.

The hollow portion 110 is a pathway through which a suture is inserted and pass. The hollow portion 110 may have a shape or size corresponding to the circumference of the suture or may be formed to be larger in size than the size or diameter of the suture.

The removal cut 200 is a cut to which waste forming under the epidermis may be introduced. The removal cut 200 may be formed at a position about 1 mm to 2 mm away from the insertion portion 300.

The removal cut 200 may have a predetermined depth from the outer circumferential surface of the body 100 to the hollow portion 110. A surface of the removal cut 200 may be formed to be perpendicular to a longitudinal direction of the body 100. Another surface of the removal cut 200 may be formed to be inclined towards the insertion portion 300 or in an opposite direction of the insertion portion 300. The removal cut 200 may be shaped as the letter "V."

The removal cut 200 may be formed to have various sizes. A plurality of removal cuts 200 may be formed.

The insertion portion 300 may cut the skin to allow the body 100 to be inserted. The insertion portion 300 may be formed at an end of the body 100. The insertion portion 300 may include a first inclined edge 310, a second inclined, edge 320, and a third inclined edge 330.

The first inclined edge 310 may be a surface inclined downwards from an end of the body 100 towards the hollow portion 110. The first inclined edge 310 may be formed in a longitudinal direction of the body 100 to be longer than the second inclined edge 320 and the third inclined edge 330.

The second inclined edge 320 may be an inclined surface formed to be inclined upwards from another end of the body 100 of the first inclined edge 310 to the first inclined edge 310. The second inclined edge 320 may come in tight contact with the hypodermis, when inserted to the skin, to support the body 100 against the hypodermis. The third inclined edge 330 may be an inclined surface formed to be inclined downwards from an end of the first inclined edge 310 to the second inclined edge 320 The third inclined edge 330 may be formed between the first inclined edge 310 and the second inclined edge 320. The third inclined edge 330 may uphold the hypodermis when inserted into the skin.

The end where the second inclined edge 320 and the third inclined edge 330 meet may be formed as a straight line, such as a straight line of as sharp blade.

When the bio paracentesis needle 10 is inserted into the skin, the second inclined edge 320 may support the body 100 against the hypodermis, and the third inclined edge 330 may uphold the tissues of the epidermis. Thus, the bin paracentesis needle 10 may be inserted shallow without escaping between the epidermis and the hypodermis.

Figure 3:
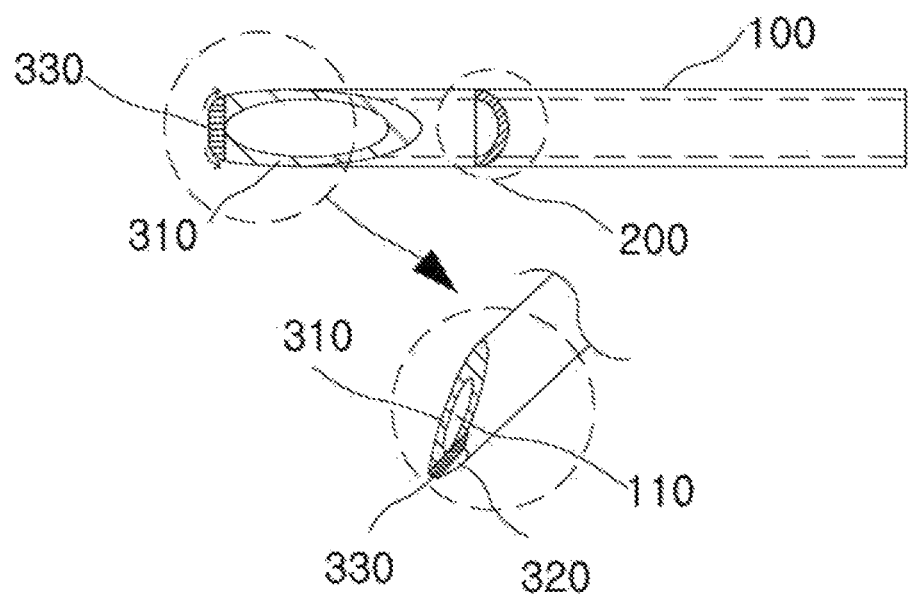
FIG. 3 is a view illustrating a bio paracentesis needle with a rounded second inclined edge and a rounded third inclined edge according to an embodiment of the present disclosure.

FIG. 3 is a view illustrating a bio paracentesis needle with a rounded second inclined edge and a rounded third inclined, edge according to an embodiment of the present disclosure.

Referring to FIG. 3, the second inclined edge 320 and the third inclined edge 330 each may have two opposite rounded sides or edges towards the hollow portion 110.

The rounded edges may be spaced apart from the hollow portion 110 at a predetermined distance. The rounded edges may have steeply or gently curved shapes. The rounded edges may be formed, e.g., by a method of cutting in a direction of the body 100 or a polishing method. The rounded edges may minimize skin scars that may occur when the insertion portion 300 incises the skin and is inserted into the skin.

Figure 4:
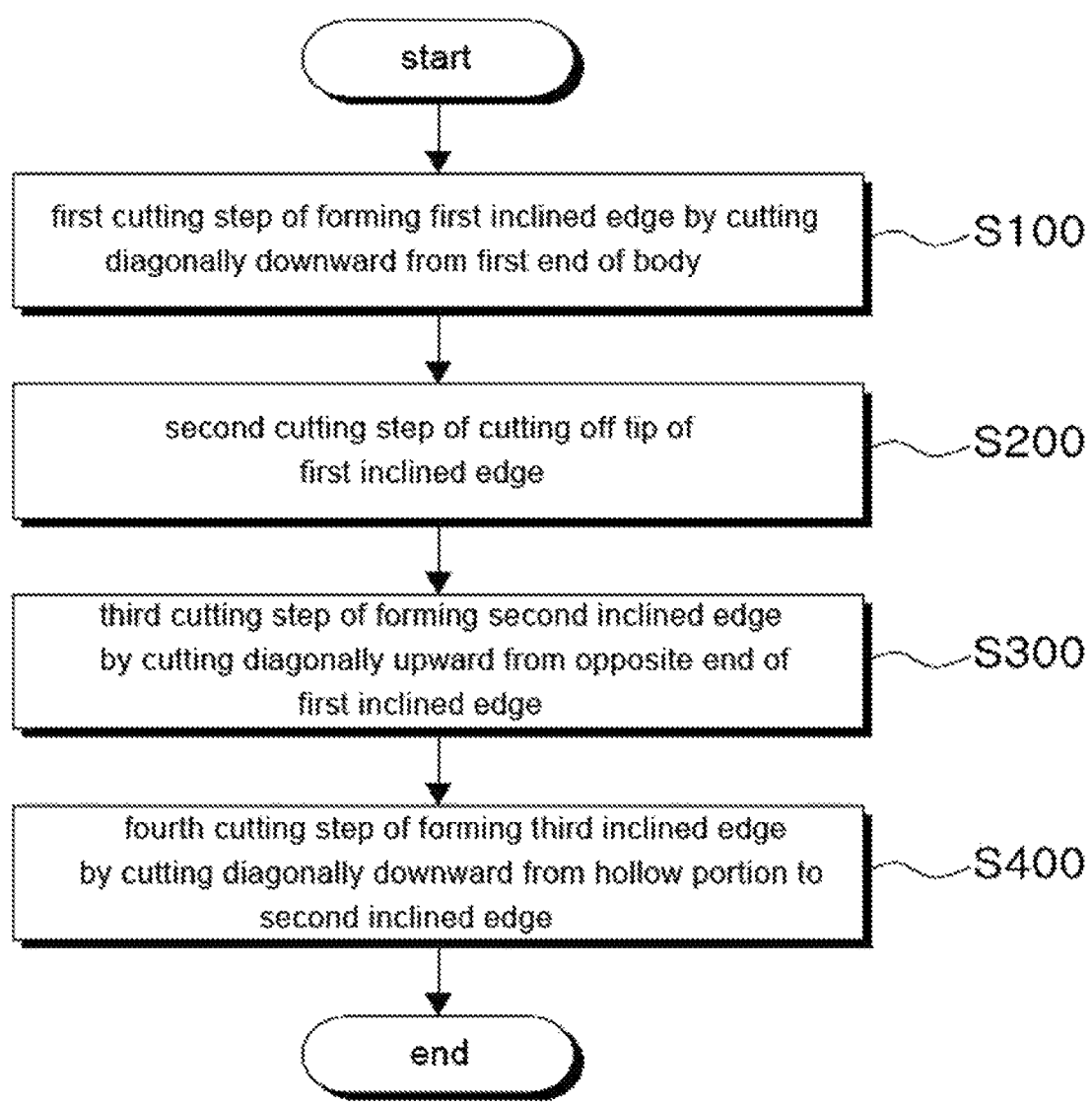
FIG. 4 is a flowchart illustrating a method for manufacturing a bin paracentesis needle according to an embodiment of the present disclosure.

FIG. 4 is a flowchart illustrating a method for manufacturing a bin paracentesis needle according to an embodiment of the present disclosure. FIGS. 5 to 8 are views illustrating a method for manufacturing a bio paracentesis needle according to an embodiment of the present disclosure.

Referring to FIGS. 4 to 8, a method for manufacturing a bin paracentesis needle having a body shaped as a tube and a hollow portion through which a suture is inserted may include a first cutting step S100 of forming a first inclined edge by cutting an end of the body in a direction inclined downward from a first end of the body, a second cuffing step S200 of cutting off an end of the first inclined edge, a third cutting step S300 of forming a second inclined edge by cutting the body in a direction inclined upward from a second end of the body, which is positioned opposite the first end of the body, and a fourth cutting step S400 of forming a third inclined edge by cutting the first inclined edge in a direction inclined downward from the hollow portion to the second inclined edge.

Figure 5:
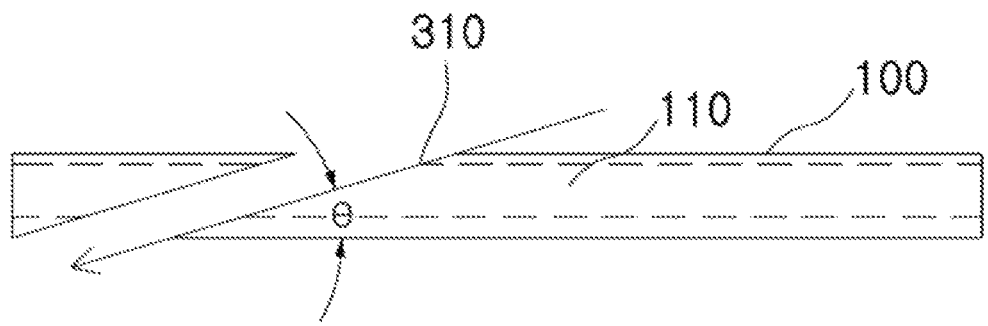
FIGS. 5 to 8 are views illustrating a method for manufacturing a bio paracentesis needle according to an embodiment of the present disclosure.

In the first cutting step S100, as shown in FIG. 5, the body 100 may be diagonally cut downward in a direction from an end thereof to the hollow portion 100, forming the first inclined edge 310, The angle θ of the cutting may be about 14.5 degrees to about 16.5 degrees. For example, the angle θ may be an angle between the first inclined edge 310 and a bottom of the body 100, e.g., as viewed from FIG. 5.

Figure 6:
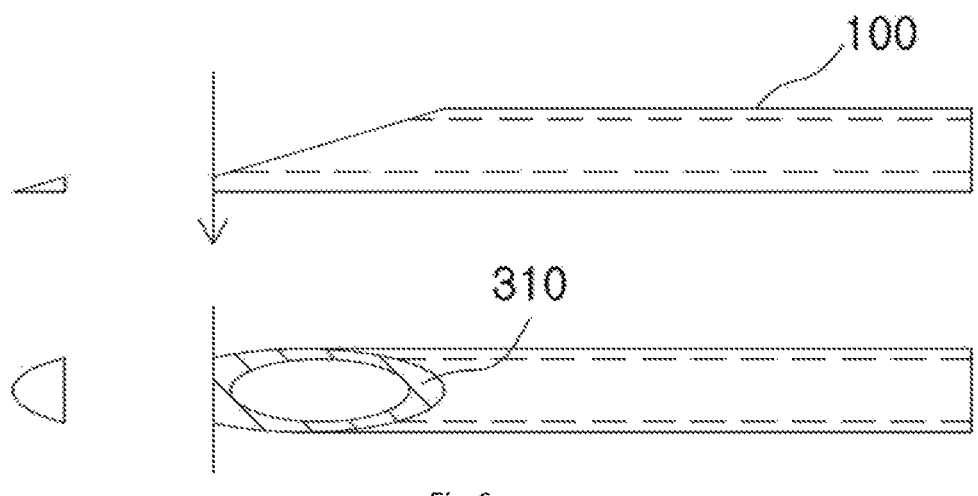

In the second cutting step S200, as shown in FIG. 6, an end or tip of the first inclined edge 310 may be cut off in a direction substantially perpendicular to the outer circumferential surface of the body 100, allowing, a front edge or end of the body 100 or the first inclined edge 310 to form a straight line shape.

The end or tip cut of the first inclined edge 310 in the second cutting step S200 may be about 2 mm to about 3 mm long.

Figure 7:
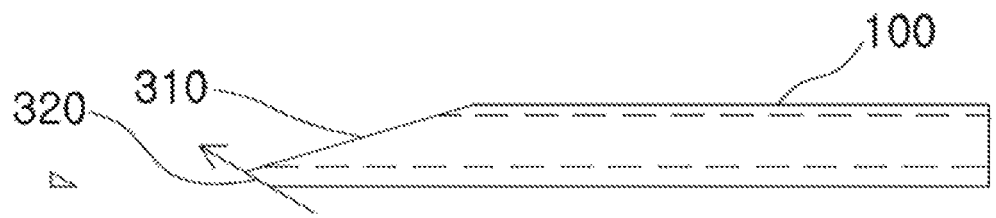

In the third cutting step S300, as shown in FIG. 7, the first inclined edge 310 ma be diagonally cut upward in a direction from another end of the body 100 to the first inclined edge 310, forming the second inclined edge 320.

Figure 8:
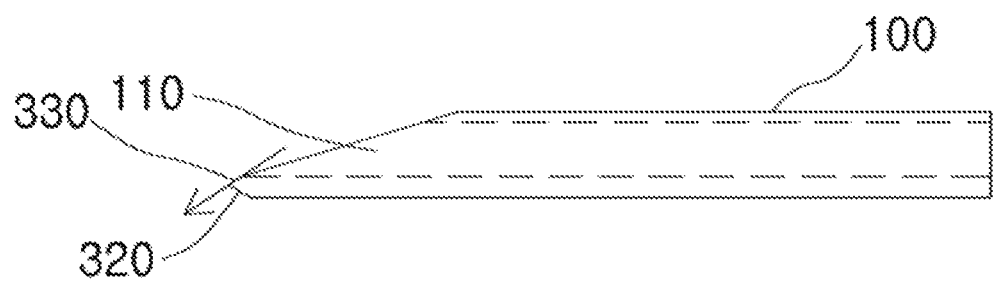

In the fourth cutting step S400, as shown in FIG. 8, the first inclined edge 310 may be diagonally cut downward in a direction from the hollow portion 110 to the second inclined edge 320, forming the third inclined edge 330, the third inclined edge 330 may be formed between the first inclined edge 310 and the second inclined edge 320.

The method for manufacturing a bio paracentesis needle may further include a fifth cutting step of forming a removal cut by cutting the body 100 in a direction from the outer circumferential surface of the body 100 to the hollow portion 110. The fifth cutting step may be included before or after any one of the first cutting step S100 through the fourth cutting step S400.

A surface of the removal cut 200 may be formed substantially perpendicular to the longitudinal direction of the body 100. Another surface of the removal cut 200 may be formed to be inclined in an opposite direction of the first inclined edge 310.

The method for manufacturing a bio paracentesis needle may further include a rounding step of rounding two opposite sides of the second inclined edge 320 and the third inclined edge 330 towards the hollow portion 110. The rounding step may be included after the fourth cutting step S400.

Herein, the rounding step may be performed, e.g., by cutting or polishing the two opposite sides of the second inclined edge 320 and the third inclined edge 150 in a direction to the body 100.

According to embodiments of the present disclosure, the bio paracentesis needle has a sharp, straight blade at a tip of the body, allowing the needle to be inserted shallow along skin wrinkles.

While the inventive concept has been shown and described with reference to exemplary embodiments thereof it will be apparent to those of ordinary skill in the art that various changes in form and detail may be made thereto without departing from the spirit and scope of the inventive concept a defined by the following claims.

What is claimed is:

1. A bio paracentesis needle, comprising:
a tube-shaped body having a hollow portion;
an insertion portion formed at an end of the body and configured to cut skin so as for the body to be inserted into the skin; and
at least one removal cut configured for removing waste under the skin when the body is inserted, the removal cut being extended to an inside of the body and disposed on the body at a distance from the insertion portion,
wherein the insertion portion includes:
a first inclined edge having a diagonal surface inclined downward in a direction from a top position of an outside surface of the body to the hollow portion;
a second inclined edge having a diagonal surface inclined upward in a direction from a bottom position of the outside surface of the body to the hollow portion; and
a third inclined edge having a diagonal surface inclined downward in a direction from an end of the first inclined edge to an end of the second inclined edge, a proximal end of the third inclined edge meeting the end of the first inclined edge and a distal end of the third inclined edge meeting the end of the second inclined edge,
wherein a first surface of the removal cut is formed perpendicular to a longitudinal direction of the body, and a second surface of the removal cut is formed to be inclined in an opposite direction of the insertion portion, and
wherein the distal end of the third inclined edge is formed in a straight line perpendicular to the longitudinal direction of the body, and the proximal end of the third inclined edge is formed in a straight line perpendicular to the longitudinal direction of the body to be in parallel with the distal end of the third inclined edge.

2. The bio paracentesis needle of claim 1, wherein the removal cut is formed in a shape of "V".

3. The bio paracentesis needle of claim 1, wherein two opposite sides of the second inclined edge and the third inclined edge are rounded towards the hollow portion.

4. The bio paracentesis needle of claim 1, wherein the body is curved or bent.

5. A bio paracentesis needle, comprising:
a tube-shaped body having a hollow portion;
an insertion portion formed at an end of the body and configured to cut skin so as for the body to be inserted into the skin; and
at least one removal cut configured for removing waste under the skin when the body is inserted, the removal cut being extended to an inside of the body and disposed on the body at a distance from the insertion portion,
wherein the insertion portion includes:
a first inclined edge having a diagonal surface inclined downward in a direction from a top position of an outside surface of the body to the hollow portion;
a second inclined edge having a diagonal surface inclined upward in a direction from a bottom position of the outside surface of the body to the hollow portion; and
a third inclined edge having a diagonal surface inclined downward in a direction from an end of the first inclined edge to the second inclined edge, a proximal end of the third inclined edge meeting the end of the first inclined edge and a distal end of the third inclined edge meeting the end of the second inclined edge,
wherein a first surface of the removal cut is formed perpendicular to a longitudinal direction of the body, and a second surface of the removal cut is formed to be inclined in a direction of the insertion portion, and
wherein the distal end of the third inclined edge is formed in a straight line perpendicular to the longitudinal direction of the body, and the proximal end of the third inclined edge is formed in a straight line perpendicular to the longitudinal direction of the body to be in parallel with the distal end of the third inclined edge.

6. The bio paracentesis needle of claim 2, wherein two opposite sides of the second inclined edge and the third inclined edge are rounded towards the hollow portion.

7. A method for manufacturing a bio paracentesis needle having a tube-shaped body shaped and a hollow portion, the method comprising:
forming a first inclined edge by cutting the body in a direction inclined downward from a first end of the body to the hollow portion;
cutting the first inclined edge perpendicular to an outer circumferential surface of the body;
forming a second inclined edge by cutting the body in a direction inclined upward from a second end of the body to the first inclined edge, the second end positioned opposite the first end:
forming a third inclined edge by cutting the body in a direction inclined downward from the hollow portion to the second inclined edge, such that a proximal end of the third inclined edge meets an end of the first inclined edge and a distal end of the third inclined edge meets an end of the second inclined edge; and
forming a removal cut in a direction from the outer circumferential surface to the hollow portion,
wherein a first surface of the removal cut is formed perpendicular to a longitudinal direction of the body, and a second surface of the removal cut is formed to be inclined in a direction or an opposite direction of the first inclined edge, and
wherein the distal end of the third inclined edge is formed in a straight line perpendicular to the longitudinal direction of the body, and the proximal end of the third inclined edge is formed in a straight line perpendicular to the longitudinal direction of the body to be in parallel with the distal end of the third inclined edge.

8. The method of claim 7, further comprising rounding two opposite sides of the second inclined edge and the third inclined edge towards the hollow portion.

* * * * *